US008999399B2

(12) United States Patent
Lisowsky et al.

(10) Patent No.: US 8,999,399 B2
(45) Date of Patent: Apr. 7, 2015

(54) COMBINED DISINFECTION AND DECONTAMINATION AGENT HAVING INCREASED EFFECTIVENESS

(75) Inventors: Thomas Lisowsky, Monheim (DE);
Sven Eggerstedt, Hamburg (DE);
Richard Bloss, Rellingen (DE);
Christiane Ostermeyer, Hamburg (DE);
Karlheinz Esser, Monchengladbach (DE); Frank Bürger, Düsseldorf (DE);
Barbara Krug, Hamburg (DE); Yvonne Feil, Kiel (DE); Kai-Martin Mueller, Hamburg (DE); Delphine Haase, Wentorf (DE)

(73) Assignee: Bose Chemie GmbH, Hamburg (DE)

( * ) Notice: Subject to any disclaimer, the term of this patent is extended or adjusted under 35 U.S.C. 154(b) by 343 days.

(21) Appl. No.: 13/140,436

(22) PCT Filed: Nov. 14, 2009

(86) PCT No.: PCT/EP2009/008122
§ 371 (c)(1),
(2), (4) Date: Aug. 25, 2011

(87) PCT Pub. No.: WO2010/078883
PCT Pub. Date: Jul. 15, 2010

(65) Prior Publication Data
US 2012/0107415 A1    May 3, 2012

(30) Foreign Application Priority Data
Dec. 18, 2008 (DE) .................. 10 2008 064 481

(51) Int. Cl.
| | | |
|---|---|---|
| *A01N 31/02* | (2006.01) | |
| *A01N 33/12* | (2006.01) | |
| *A01N 35/02* | (2006.01) | |
| *A01N 31/08* | (2006.01) | |
| *A01N 31/10* | (2006.01) | |
| *A01N 31/16* | (2006.01) | |
| *A01N 27/00* | (2006.01) | |
| *A01N 59/00* | (2006.01) | |
| *A01N 59/14* | (2006.01) | |
| *A01N 37/16* | (2006.01) | |
| *A61K 31/045* | (2006.01) | |
| *A61K 31/047* | (2006.01) | |
| *A61K 31/19* | (2006.01) | |
| *A61K 31/14* | (2006.01) | |
| *A61K 31/11* | (2006.01) | |
| *A61P 31/00* | (2006.01) | |
| *A01N 37/36* | (2006.01) | |
| *A01N 59/16* | (2006.01) | |
| *A01N 43/08* | (2006.01) | |
| *A01N 59/20* | (2006.01) | |

(52) U.S. Cl.
CPC ............ *A01N 59/16* (2013.01); *A01N 43/08* (2013.01); *A01N 59/20* (2013.01)

(58) Field of Classification Search
None
See application file for complete search history.

(56) References Cited

U.S. PATENT DOCUMENTS

| | | | | |
|---|---|---|---|---|
| 4,477,438 A | * | 10/1984 | Willcockson et al. | 424/616 |
| 4,929,365 A | * | 5/1990 | Clark et al. | 210/754 |
| 6,296,881 B1 | | 10/2001 | Hata et al. | |
| 2005/0238602 A1 | * | 10/2005 | Modak et al. | 424/70.11 |
| 2005/0267109 A1 | * | 12/2005 | Holzl et al. | 514/241 |
| 2007/0264353 A1 | * | 11/2007 | Myntti et al. | 424/600 |
| 2009/0076084 A1 | | 3/2009 | Krug et al. | |
| 2010/0119566 A1 | | 5/2010 | Krug et al. | |

FOREIGN PATENT DOCUMENTS

| | | | | |
|---|---|---|---|---|
| DE | 19936428 | | 2/2000 | |
| DE | 29903417 | | 7/2000 | |
| DE | 19910355 | | 9/2000 | |
| DE | 102005020327 | | 11/2006 | |
| EP | 0255875 | * | 7/1987 | ............. A01N 35/02 |
| EP | 0 987 300 | | 12/1998 | |
| EP | 2077260 | * | 7/2009 | ........... C07D 207/14 |
| WO | PCT/EP98/03147 | | 12/1998 | |
| WO | WO01/28339 | | 4/2001 | |
| WO | WO2008/068533 | * | 6/2008 | ............. A01N 59/20 |
| WO | WO2008/089822 | | 7/2008 | |
| WO | WO2009/003991 | | 1/2009 | |
| WO | WO2009/133616 | | 11/2009 | |

OTHER PUBLICATIONS

Musk, D. J. et al. "Iron salts perturb biofilm formation and disrupt existing biofilms of *Pseudomonas aeruginosa*" Chemistry & Biology, 2005, 12, 789-796.*
International Search Report, dated Oct. 27, 2010, issued in corresponding PCT application PCT/EP2009/008122, 6 pages.
PCT International Preliminary Report on Patentability, dated Jun. 21, 2011, issued in corresponding PCT application, PCT/EP2009/008122, 10 pages.
Wallháußer, Karl Heinz: Praxis der Sterilisation Desinfektion—Konservierung 3. Aufl. Stuttgart; New York:1984, Inhaltsverzeichnis S.XIX-XXI; ISBN 3-13-416303-p.
English translation of Wallháußer, Karl Heinz: Praxis der Sterilisation Desinfektion—Konservierung 3. Aufl. Stuttgart; New York:1984, ISBN 3-13-416303-p.

* cited by examiner

*Primary Examiner* — Mina Haghighatain
*Assistant Examiner* — Erin Hirt
(74) *Attorney, Agent, or Firm* — Nash and Titus, LLC

(57) ABSTRACT

The invention relates to a novel combined disinfection and decontamination agent comprising at least one vitamin, at least one metal ion, at least one active-surface compound, and at least one further antimicrobial active substance. The agent according to the invention surprisingly shows nearly complete nucleic acid disintegration in addition to an improved disinfectant effect. The agent can be successfully used as a combined decontamination and disinfection agent for skin, mucous membranes, hands, wounds, and/or hair, and instruments and surfaces of all kinds.

16 Claims, No Drawings

COMBINED DISINFECTION AND DECONTAMINATION AGENT HAVING INCREASED EFFECTIVENESS

BACKGROUND OF THE INVENTION

This application is a 371 national filing claiming priority from international application PCT/EP2009/008122, filed Nov. 14, 2009. This application also claims priority from German application 10 2008 064 481.1, filed Dec. 18, 2008. The entire contents of that international application and that German application are incorporated herein by reference.

The invention has as subject matter a disinfection and decontamination agent containing at least one vitamin, at least one metal ion, at least one surface-active compound and at least one antimicrobial active substance.

It is necessary in the medicinal area, in the production of food, in test laboratories and in other sensitive areas to kill microorganisms and to remove them as completely as possible. It is known on the one hand to combat the microorganisms in the form of a disinfection. The term disinfection generally denotes the effective, irreversible inactivation, killing or removal of microorganisms. Microorganisms include bacteria, mycobacteria, fungi, yeasts, spores, prions, mycoplasms and/or viruses. The latter are removed during the disinfection of animated and/or inanimate surfaces, tissues or rooms.

It turned out in a few areas that a disinfection alone is not sufficient, since even the killed microorganisms or individual nucleic acid molecules such as DNA and RNA of the microorganisms or proteins or other residues can result in further infections directly or by increasing the infectiousness or resistance of other microorganisms. Therefore, decontamination agents are used for the complete elimination of the contamination with proteins or nucleic acids. The DNA/RNA decontamination agents should bring about a nucleic acid degradation that is as complete as possible for an effective decontamination.

It is therefore necessary in a complete disinfection and decontamination of an animated or inanimate surface to use two agents, namely, a disinfection agent for killing the microorganisms and a decontamination agent for eliminating the remaining residual contamination by nucleic acid molecules, proteins or other residues. The use of a decontamination agent ensures the efficient decontamination in that the free nucleic acid molecules are modified, denatured or degraded. The known decontamination agents have the disadvantage that they frequently are chemically aggressive and not absolutely safe for health. During the use of aggressive substances they attack, for example, inanimate surfaces and result in permanent damage or discoloration. On animated surfaces such as hands, skin, mucous membranes many aggressive decontamination agents cannot be used at all for reasons of health.

A less aggressive decontamination agent is known, for example from DE 10 2005 020 327 A1. This decontamination solution consisting of a vitamin, a metal ion and a surface-active compound displays a good nucleic acid degradation while simultaneously gently treating the surfaces. However, for example, no sufficient effectiveness in the customary application concentrations and acting times against *Candida albicans* was able to be determined.

SUMMARY OF THE INVENTION

Therefore, the present invention addresses the problem of making a novel combination agent available that brings about for the first time a simultaneous disinfection and decontamination of animated and inanimate surfaces. The agent should protect surfaces, i.e., should have good compatibility with materials and be compatible with skin and mucous membranes. In addition to a reliable disinfection the agent should display a degradation of nucleic acids which is as complete as possible.

The problem is solved in accordance with the invention by a disinfection- and decontamination agent containing at least one vitamin, at least one metal ion, at least one surface-active compound and at least one antimicrobial active substance, whereby the antimicrobial active substance is selected from the group consisting of:
- monovalent or multivalent, aliphatic or aromatic and/or substituted alcohols,
- quaternary ammonium compounds,
- aliphatic or aromatic mono- or dialdehydes,
- phenols or phenol derivatives,
- aliphatic secondary or tertiary amines,
- peroxides or peracids,
- organic and inorganic acids or their salts, esters or amides,
- guanidines or biguanides,
- pyridines or pyrimidines,
- amphoteric active substance according to the regulation (EC) No. 1451/2007 of the commission of Dec. 4, 2007 selected from the group of
- amines, n-C10-16-alkyltrimethylene di-, reaction products from chloroacetic acid (AMPHOLYT 30),
- quaternary ammonium compounds, [2-[[2-[(2-carboxyethyl)(2-hydroxyethyl)amino]ethyl]amino]-2oxyethyl] coconut alkyldimethyl-, their hydroxides, their "inner salts" (Rewoteric QAM 50),
- N-[3-(dodecylamino)propylglycine (Amphionic SFB),
- isothiazolines,
- ethereal oils or
- a mixture of these.

Further embodiments are subject matter of the subclaims or are described in the following description.

DETAILED DESCRIPTION OF THE PREFERRED EMBODIMENTS

If alcoholic active substances are used as antimicrobial active substance, they are preferably monovalent alcohols such as methanol, ethanol, 1-propanol, 2-propanol, butanol, chlorobutanol, pentanol or hexanol or a mixture of them, especially preferably ethanol, 1-propanol, 2-propanol, butanol and/or pentanol. The monovalent alcohols are used as antimicrobial active substance in a concentration of 1-90%, preferably 1.5-80% and especially 2-70 wt. %. Compounds with 2 to 80 wt. %, preferably 2 to 40 wt. % and 2 to 30 wt. % monovalent alcohol proved to be especially suitable.

E.g., propylene glycol, polyethylene glycol, triethylene glycol, hexyldiglycol, butylene glycol, pentane diol, hexane diol, heptane diol, octane diol, decane diol, glycerol, preferably as 1,2- or 1,3-diols or hexyldiglycol or mixtures of them are used, especially preferably propylene glycol, polyethylene glycol, hexyldiglycol, butylene glycol, pentane diol, hexane diol, heptane diol and/or octane diol. This preferably takes place in a concentration of 0.01-20 wt. %, especially preferably 0.025-15 wt. % and especially 0.025-10 wt. % and especially 0.05-5.0%.

If aromatic alcohols are used as antimicrobial active substance, they are preferably benzyl alcohol, chlorobenzyl alcohol, phenylethyl alcohol, phenoxy ethanol, 1,2-phenoxy propanol, 1,3-phenoxy propanol and/or mixtures of them, especially preferably phenoxy ethanol. They are preferably used in concentrations of 0.01-15 wt. %, especially preferably 0.02-15 wt. % and in particular 0.02-10 wt. % and in particular 0.02-5.0 wt. %.

For example, 2-bromo-2-nitro propane diol (Bronopol), 5-bromo-5-nitro-1,3-dioxane (Bronidox) are used as substituted alcohols. They are used in concentrations of 0.01-20 wt. %, especially preferably 0.025-15 wt. % and especially 0.05-10 wt. % and especially 0.05-5.0 wt. %.

In a further embodiment the antimicrobial active substance is a quaternary ammonium compound. Suitable quaternary ammonium compounds are, for example, didecyldimethyl ammonium chloride (DDAC), benzalconium chloride (BAC), benzalconium bromide, benzoxonium chloride, dioctyldimethyl ammonium chloride, N,N-dialkyl-N,N-dimethylammonium carbonate, quaternary ammonium iodides, quaternary ammonium compounds of the type dialkyldimethyl (alkyl from C6-C18, saturated and unsaturated, and tallow alkyl, coconut alkyl and soybean alkyl) chlorides, bromides or methyl sulfates/DDAC, mecetronium ethyl sulfate (MES), dimethyldecyloxethyl ammonium propionate, cetrimides, cetrimonium bromide, cetylpyridinium chloride or undecylene amidopropyltrimonium methosulfate. Didecyldimethyl ammonium chloride (DDAC), benzalconium chloride (BAC) or mecetronium ethyl sulfate (MES) are especially preferably used as antimicrobial active substance. They are preferably used in a concentration of 0.01-25 wt. %, especially preferably 0.01-20 wt. % in particular 0.01-15 wt. %. The quaternary ammonium compounds are furthermore preferably used in concentrations of 0.01-10 wt. %, especially preferably 0.01-5.0 wt. % and in particular 0.01-2 wt. %.

In a further embodiment the antimicrobial active substance used in the disinfection- and decontamination agent of the invention is an aldehyde selected from the group of aliphatic or aromatic mono- or dialdehydes. Suitable mono- and dialdehydes are in particular glutardialdehyde, succinic dialdehyde, ortho-phthalaldehyde, glyoxal, acrolein, piperonal, formaldehyde, formaldehyde eliminators and eliminators of dialdehydes. Formaldehyde eliminators, are e.g., (ethylene dioxyl)dimethanol, tetrahydro-1,3,4,6-tetrakis(hydroxymethyl)imidazo[4,5-d]imidazone-2,5(1H,3H)-dione, imidazolidinyl urea, 1,3-bis(hydroxymethyl)urea, diazolidinyl urea, triazines, paraformaldehyde, hexamethylene tetraamine, Quaternium® 15 or dimethyloldimethyl hydantoin. The monoaldehydes and/or dialdehydes are preferably used in concentrations of 0.01-15 wt. %, especially preferably 0.1-10 wt. % and in particular 0.01-5.0 wt. %, in particular 0.025-2.5 wt. %.

Other suitable antimicrobial active substance are phenols and phenol derivatives such as, e.g., phenol, pentachlorophenol, cresol, chlorocresol, 4-chloro-3,5-dimethylphenol, thymol, eugenol, resorcinol, 4-hexylresorcinol, biphenyl, 2-phenylphenol, chlorophene, dichlorophene, hexachlorophene, triclosane, bromochlorophene, xylenols, chloroxylenols, isopropyl cresols, chlorothymols, or their mixtures, preferably thymol, 2-phenylphenol or triclosane. They are preferably used in a concentration of 0.01-20 wt. %, especially preferably 0.05-15 wt. % and in particular 0.01-10 wt. % and in particular 0.1-5.0%.

In a further embodiment the antimicrobial active substance is an aliphatic or aromatic organic acid or an inorganic acid or its salt, ester or amide. Suitable organic acids are, for example, formic acid, acetic acid, bromoacetic acid, glycolic acid, propionic acid, glyoxylic acid, lactic acid, citric acid, tartaric acid, malonic acid, maleic acid, fumaric acid, pyrrolidone carboxylic acid, sorbic acid, undecenoic acid, undecynoic acid, benzoic acid, hydroxybenzoic acid, salicylic acid, dehydracetic acid, 4-hydroxybenzoic acid ester (parabene), dimethyl carbonate, chloroacetamide, 2-chloro-N-(hydroxymethyl)acetamide and/or salicylic anilide, preferably glycolic acid, lactic acid, citric acid, pyrrolidone carboxylic acid, sorbic acid, undecylenoic acid, hydroxybenzoic acid, salicylic acid, dehydracetic acid and/or 4-hydroxybenzoic acid ester (parabene). The organic acid is preferably used in a concentration of 0.01-10 wt. % or 0.01-5.0 wt. %, especially preferably 0.01-3.0 wt. % and in particular 0.01-2.4 wt. % or 0.025-2.5 wt. %. Suitable inorganic acids are, for example, phosphoric acid, sulfuric acid, hydrochloric acid, boric acid, sulfurous acid, nitric acid, or carbonic acid. The inorganic acids are preferably used in the same concentrations as the organic acids.

In another embodiment the antimicrobial active substance is a peroxide or a peracid, whereby preferred peroxides or peracids are selected from the group of hydrogen peroxide, benzoyl peroxide, peracetic acid, sodium perborate, magnesium monoperoxyphthalate or magnesium monoperoxyphthalate hexahydrate (MMPP), pentapotassium bis(peroxymonosulfate)bis(sulfate), disodium peroxodisulfate/sodium persulfate, dipotassium peroxodisulfate, disodium carbonate with hydrogen peroxide, 2-butanone peroxide, tert-butylhydroperoxide, peroxyoctanoic acid, peracid ester or the reaction product from dimethyl adipate, dimethylglutarate, dimethylsuccinate with hydrogen peroxide, e.g., Perestane® (Solvay) and/or phthalimide-peroxy-caproic acid, 6-(phthalimide)peroxyhexanoic acid, preferably hydrogen peroxide or magnesium monoperoxyphthalate (MMPP). The peroxides are preferably used in a concentration of 0.01-10 wt. % or 0.01-5.0 wt. %, more preferably from 0.01-2.0 wt. %, especially preferably 0.01-1.0 wt. % and in particular 0.01-0.5 wt. %.

In a further embodiment the antimicrobial active substance is a guanidine-, biguanide- or pyridine or pyrimidine compound such as, for example, a chlorohexidine salt such as, e.g., digluconate (CHG), polyhexanide, PHMG, coconut propylene diamine-1,5-bisguanidium acetate, dipyrithione, pyrithione zinc, piroctone, hexetidine or octenidine salt such as, e.g., dihydrochloride and monoperoxyphthalate. These active substances are used, for example, in a concentration of 0.01-20 wt. %, preferably 0.01-10 wt. %, as well as 0.01-5.0 wt. %, whereby preferably concentrations of 0.01-2.0 wt. %, especially preferably 0.01-1.5 wt. % and in particular 0.05-1.0 wt. % or 0.05-0.5 wt. % are used.

In a further embodiment the antimicrobial active substance is an aliphatic secondary or tertiary amine such as, for example, an N-(3-aminopropyl)-N-dodecyl propane-1,3-diamine, N-dodecyl propane-1,3-diamine or a conversion product of L-glutamic acid and coconut propylene-1,3-diamine as is sold under the trademark Glucoprotamin®. The aliphatic amines are preferably used in a concentration of 0.01-25 wt. %, preferably 0.01-20 wt. %, as well as 0.01-15 wt. %, whereby concentrations of 0.01-10 wt. %, especially preferably 0.01-5.0 wt. % and in particular 0.01-2.0 wt. % are preferably used.

In another embodiment of the antimicrobial active substance an amphoteric active substance according to regulation (EC) No. 1451/2007 of the commission of Dec. 4, 2007 is selected from the group consisting of n-C-10C16-alkyltrimethylene diamine-, reaction products from chloroacetic acid (AMPHOLYT 30) or reaction product from 1,3-propane diamine, C10C16 alkyl derivative and chloroacetic acid or amine, n-C10-16-alkyltrimethylene di-, reaction products from chloroacetic acid (or aminoalkyl glycines), quaternary ammonium compounds [2-[[2-[(2-carboxyethyl)(2-hydroxyethyl)amino] ethyl]amino]-2oxyethyl]coconut alkyldimethyl-, their hydroxides, their "inner salts" (Rewoteric QAM 50), or cocobetaine amdoamphopropion, N-[3-(dodecylamino)propyl-glycine hydrochloride (amphionic SFB) or alkylamino carboxylate. The amphoteric compound is preferably used in a concentration of 0.01-25 wt.%, especially preferably 0.01-20 wt. % and in particular 0.01-15 wt. %, 0.01-10 wt. %, especially preferably 0.01-5.0 wt. % and in particular 0.01-2.0 wt. %.

In another embodiment the antimicrobial active substance is an ethereal oil such as, for example, citronellol, linalool (e.g., lavender oil), geraniol (e.g., rose oil), cinnamaldehyde (e.g., cinnamon oil), tea tree oil, camphor, menthol, farnesol or pine extract. The ethereal oils are preferably used in the concentration of 0.002-5.0 wt. % or 0.002-1.0 wt. %, especially preferably 0.005-0.5 wt. % and in particular 0.002-0.1 wt. %.

In another embodiment the antimicrobial active substance is an isothiazoline such as, e.g., methyl isothiazolinone, chloromethylisothiazolinone, octylisothiazolinone. The isothiazolines are preferably used in a concentration of 0.001-1 wt. %, preferably 0.005-0.5 wt. %, especially preferably 0.005-0.2 wt. % and in particular 0.005-0.1 wt. %.

The disinfection- and decontamination agent in accordance with the invention contains especially preferably one or more antimicrobial active substances, whereby the following are used as preferred active substances: ethanol, 1-propanol, 2-propanol, butanol, pentanol, propylene glycol, polyethylene glycol, hexyldiglycol, butylene glycol, 1,2-pentane diol, 1, 2 hexane diol, heptane diol, 1,2-octane diol, 1,2-decane diol, lactic acid, salicylic acid, glycolic acid, citric acid, pyrrolidone carboxylic acid, sorbic acid, undecenoic acid, hydroxybenzoic acid, salicylic acid, dehydracetic acid, 4-hydroxybenzoic acid ester (parabene), phosphoric acid, hydrochloric acid, chlorohexidine salts, polyhexanide, PHMG, octenidine salts, pyrithione zinc, phenoxy ethanol, didecylmethyl ammonium chloride (DDAC), benzalkonium chloride (BAC), mecetronium ethyl sulfate (MES), glutardialdehyde, thymol, 2-phenylphenol, triclosane, hydrogen peroxide, magnesium monoperoxyphthalate (MMPP), or their mixture.

The vitamin used in the disinfection agent of the invention, whose salt or acidic derivative is preferably a vitamin with the property of antioxidants. Suitable vitamins are in particular vitamin A, vitamin C (D-ascorbic acid), B and E. Especially preferred vitamins are the water-soluble vitamins B and C. The vitamin is contained in the disinfection- and decontamination agent in accordance with the invention in amounts of 0.1 mM to 1000 mM, especially preferably 0.1 mM to 500 mM, more preferably 0.1 mM to 300 mM and in particular 0.1 mM to 100 mM in the disinfection- and decontamination agent in accordance with the invention.

An ion of a metal of the fourth period or an ion of a metal of subgroups I., II. or VIII. of the periodic table of elements is used as metal ion in the disinfection- and decontamination agent in accordance with the invention. Especially preferred metal ions are iron, cobalt, zinc, copper and silver. The metal ion is contained in amounts of 0.01 mM to 100 mM, preferably 0.01 to 50 mM, especially 0.01 mM to 30 mM, especially preferably 0.01 mM to 10 mM in the agent in accordance with the invention.

The disinfection- and decontamination agent in accordance with the invention preferably contains as surface-active substance a compound selected from the group consisting of anionic, non-ionic, amphoteric or cationic surfactants or a mixture of them. The surface-active substance is contained in amounts of 0.01 wt. % to 35 wt. %, preferably 0.01 wt. % to 30 wt. %, in particular 0.01 wt. % to 20 wt. %, quite especially 0.025 wt. % to 15 wt. % in the entire solution. In particular, the following can be used: alkyl ether sulfates, alkyl- and/or aryl sulfonates, alkyl sulfates, amphoteric surfactants, betaines, alkylaminoalkyl amines, alkyl-substituted amino acids and/or imino acids, acylated amino acids and/or amphoteric surfactant combinations such as fatty alcohol ethoxylates, fatty alcohol propoxylates, alkylphenol polyglycol ethers, branched-chain alkyl ethoxylates, fatty acid ethoxylates, alkyl polyglucosides, saccharose esters, sorbitan esters, amino oxides. Basically, all surfactants are suitable. Anionic and non-ionic surfactants are preferred according to the invention.

All concentration data refers to the finished application solution or application form. When using non-dilute solutions the concentrations therefore indicate the amount in the non-dilute solution, when using concentrates the concentrations indicate the amount in the application solution produced from the concentrate. A corresponding situation applies to solid and semi-solid products that are dissolved in solvents for usage.

The disinfection- and decontamination agent of the invention can be used in liquid, semi-solid or solid form, whereby the following application forms are preferred: solution, suspension, emulsion, paste, gel, foam, tablet, powder, granulate, cloths, self-dissolving bag and/or two-component systems.

The disinfection- and decontamination agent of the invention can be present in the form of liquid concentrates so that a fresh solution is prepared every time. The liquid concentrates are preferably diluted with water to a solution for use.

The agent in accordance with the invention consists especially preferably of
  at least one vitamin, preferably in amounts of 0.1 mM to 1000 mM,
  at least one metal ion, preferably in amounts of 0.01 mM to 100 mM.
  at least one surface-active compound, preferably in amounts of 0.01 to 35 wt. % of the entire solution,
  at least one antimicrobial active substance,
  auxiliary substances and optionally
  water,
whereby the components supplement each other 100 wt. %. The auxiliary substances used are preferably dyes, preservation agents, emulsifiers, antioxidants, treatment substances, preservation agents, consistency imparters, solvents, thickening agents, perfume, corrosion inhibitors, complexing agents and/or pH regulators.

Suitable thickening agents are, for example, without being limited to them, polymers of acrylic acid or its derivatives such as, e.g., polyacrylic acid, acrylamide copolymer, acrylamide/sodium acrylate copolymer, acrylate copolymer, ammoniumacrylate copolymer, sodium acrylate polymer, cross-linked acrylate polymers such as, e.g., acrylates/C10-30 alkylacrylate cross polymer, carbomer, cross-linked methylmethacrylate copolymer, natural polymers and their derivatives such as, e.g., ammonium alginate, carboxymethylcellulose, carboxymethyldextran, ethylcellulose, guarhydroxypropyl trimonium chloride, hydroxyethyl chitosane, hydroxypropyl starch, hydroxypropyl starch phosphate, hydroxyethylmethyl cellulose, silicone polymers such as, e.g., cross-linked divinyldimethicone/dimethicone copolymer, polyglycols such as, e.g., polyethylene glycol, polypropylene glycol, polyethylene-co-propylene glycol with different molecular weights, polyvinyl alcohols with different molecular weight, cross-linked copolymer of methylvinyl ether/maleic acid anhydride/decadiene units (INCI: PVM/MA/decadiene cross polymer), polyvinyl pyrrolidone, and others.

The agent in accordance with the invention has a pH between 0.5 to 8.5, in particular from 1 to 7 and preferably from 2 to 6 or 2 to 4.5. In a variant a buffer system can be used for adjusting the pH. Suitable buffer systems are, for example, a buffer system with carbonates and derivatives of succinic acid, preferably in a concentration of 1 mM to 500 mM. When using this buffer system in the agent of the invention the pH of the solution, that is in the strongly acidic range on account of the dissolved components, especially on account of the acidic vitamins, can be readily raised up to, for example, the neutral or slightly basic range without the dissolved metal ions precipitating out. Suitable systems are, among others, borate-, oxalate-, phthalate-, glycine-, tartrate-, phosphate-, carbonate-, citrate-acetate buffers.

The agent in accordance with the invention is used in an embodiment for the decontamination and disinfection of animated surfaces, preferably for the disinfection and decontamination of skin, mucous membranes, wounds, hairs and/or hands. In another embodiment the agent is used for the disinfection- and decontamination of inanimate surfaces, preferably for the disinfection of instruments and/or surfaces.

It was surprisingly able to be determined that the agent in accordance with the invention performs a complete and reliable nucleic acid degradation, i.e. a complete denaturing and removal of nucleic acid molecules with a good disinfection action at the same time. The combination of the antimicrobial active substance with a combination of vitamin, metal ion and surface-active compound displays an unexpected synergism and results in a distinctly improved disinfection action compared to the individual components. Also, the action against viruses and bacteria was able to be significantly increased by a combination of metal salt, vitamin, surface-active compound and antimicrobial active substance.

In addition, the disinfection- and decontamination agent displays a distinctly better compatibility as regards material as well as skin than traditional disinfection agents. The better compatibility is conditioned, among other things, by the fact that a lesser concentration of the antimicrobial active substance can be used than in the case of customary disinfection agents due to the special synergism produced in the combination of the four active substances. This results in the better compatibility with material and skin as well as a better compatibility with the environment. The use of the antimicrobial active substance in a lesser concentration is therefore a significant advantage of the synergistic combination.

In addition, the disinfection- and decontamination agent in accordance with the invention can be used to degrade biofilms. Recent investigations have shown that medicinal instruments or implants are contaminated with microbes, whereby the contamination takes place in the form of bacterial biofilms. It surprisingly turned out that the disinfection- and decontamination agent of the invention not only eliminates isolated bacteria but also the bacteria and fungi occurring in biofilms. The examination of the degradation of biofilms was performed with a cultivated biofilm (on a silicone surface) of *Pseudomonas aeruginosa*. The acting time was 30 min at 25° C.

The use of the disinfection- and decontamination agent in accordance with the invention results in a reliable degradation of biofilms. This applies not only to the combination of metal salt, vitamin, surface-active compounds and antimicrobial active substance but also to a disinfection- and decontamination agent of metal salt, vitamin and surface-active compound. In this composition with three active substances the components metal salt, vitamin and surface-active compound can be used in the same concentrations as in the preparation with four active substances. Accordingly, even the use of a disinfection- and decontamination agent of metal salt, vitamin and surface-active compound for the degradation of biofilm is subject matter of the invention.

The advantages of the invention will be explained in detail using the following examples.

1. Virus Effectiveness

The virus effectiveness of a decontamination agent containing metal ion, vitamin and surfactant and of an alcoholic disinfection agent by way of comparison with the agent of the invention was measured. The following table shows the composition of the measured agents as well as the effectiveness of the agents to the poliovirus.

TABLE 1

Recipes of the tested solutions

| Beispiel-Nr. | M-Salz [mM] FeCl$_{3x}$6H$_2$O | :Vitamin: [mM] D-Ascorbinsäure | Tensid [%] SDS | Wirkstoffe [%] Ethanol 99% | 1-Propanol | Wasser |
|---|---|---|---|---|---|---|
| V1 | — | — | — | 40 | 20 | ad 100 |
| V2 | 5 | 50 | 0.5 | — | — | ad 100 |
| A  | 10 | 100 | 0.5 | 40 | — | ad 100 |
| V3 | 10 | 100 | 0.5 | — | — | ad 100 |
| B  | 5 | 50 | 0.5 | 40 | 20 | ad 100 |
| V4 | — | — | — | 40 | — | ad 100 |

Key:
| German | English |
|---|---|
| Beispiel-Nr. | Example No. |
| M-Salz | M salt |
| Tensid | Surfactant |
| Wirkstoffe | Active substances |

TABLE 2

Reduction factors of the tested solutions

| Beispiel-Nr. | Belastung | Konz [%] | Poliovirus 0.5 min | 1 min | 2 min | 5 min | 15 min | 60 min |
|---|---|---|---|---|---|---|---|---|
| V1 | ohne | 80 | — | — | — | 0.25 | 1.62 | 2.15 |
| V2 | ohne | 80 | — | 3.00 | — | 3.33 | 3.67 | 4.33 |
| A  | ohne | 80 | 4.00 | 4.83 | 5.83 | 6.50 | — | — |

TABLE 2-continued

| | | | | | | | | |
|---|---|---|---|---|---|---|---|---|
| V3 | ohne | 80 | 2.83 | 3.17 | 3.83 | 6.00 | — | — |
| B | ohne | 80 | — | 4.00 | — | 4.67 | 5.17 | 6.83 |
| V4 | ohne | 80 | — | — | — | 0.19 | 0.61 | 1.19 |

Key:
| German | English |
|---|---|
| Beispiel-Nr. | Example No. |
| Belastung | Load |
| Konz | Conc |
| Ohne | without |

The addition of the alcoholic active substances to the combination of metal salts, vitamins and surfactants surprisingly resulted in a distinct improvement of effectiveness against polio, although alcohols alone displayed no especially good effectiveness against polio. This is all the more noteworthy since the concentrations of alcohols are less than in the case of customary disinfection agents. Significantly shorter reaction times were able to be achieved. Thus, the agent displays a good effectiveness against viruses. In addition, it surprisingly turned out that even the degradation of nucleic acid was able to be improved upon the addition of ethanol and/or 1- and 2-propanol in comparison to the degradation of nucleic acid of the pure combination of metal salt, vitamin and surfactant. As results from table 3, the alcohols not only do not adversely affect the degradation of nucleic acid but rather even reinforce it.

TABLE 3

Results of the nucleic acid degradation tests

| Rezeptur Nr. | M-Salz [mM] $FeCl_3$ | Vitamin [mM] D-Ascorbinsäure | Tensid [%] SDS | Wirkstoff [%] Ethanol | 1-Propanol | 2-Propanol | $H_2O$ | Konz. [%] | Nukleinsäure-Abbau | |
|---|---|---|---|---|---|---|---|---|---|---|
| DNA-Ex.+ | | | | | | | | 50 | +++ | Standard |
| C | 1 | 10 | 0.5 | | 24 | 36 | ad 100 | 90 | ++ | besser |
| D | 1 | 10 | 0.5 | 30.3 | | | ad 100 | 90 | ++-+++ | |
| V5 | 1 | 10 | 0.5 | | | | ad 100 | 90 | + | Referenz |

Key:
| German | English |
|---|---|
| M-Salz | M-salt |
| Tensid | Surfactant |
| Wirkstoff | Active substance |
| Rezeptur Nr. | Recipe No. |
| D-Ascorbinsäure | D- ascorbic acid |
| Konc. | Conc. |
| Nukleinsäure-Abbau | Nucleic acid degradation |
| Besser | Better |
| Referenz | Reference |

2. Fungicidal Effectiveness

In order to determine the fungicidal effectiveness the protection of Canada albicans was measured. The following table shows the composition of the measured agents as well as the substances measured by way of comparison. The table furthermore indicates the reduction factors.

TABLE 4a

Compositions of the tested solutions

| Beispiel-Nr. | M-Salz [mM] $FeCl_{3x}$ 6H20 | Vitamin [mM] D-Ascorbinsäure | Tenside [%] SDS | Wirkstoffe [%] Ethanol | 1-Propanol | Milchsäure 90% | Wasser |
|---|---|---|---|---|---|---|---|
| V6 | 5 | 50 | 0.5 | | | | ad 100.0 |
| E | 5 | 50 | 0.5 | | | 1.00 | ad 100.0 |
| V7 | — | — | — | | | 1.00 | ad 100.0 |
| V8 | 10 | 100 | 0.5 | — | — | — | ad 100.0 |
| F | 10 | 100 | 0.5 | 40.0 | — | — | ad 100.0 |
| V9 | — | — | — | 40.0 | — | — | ad 100.0 |

Key:
| German | English |
|---|---|
| Beispiel Nr. | Example No. |
| M-Salz | M-salt |
| Tenside | Surfactants |
| Wirkstoffe | Active substances |
| D-Ascorbinsäure | D- ascorbic acid |
| Milchsäure | Lactic acid |
| Wasser | Water |

TABLE 4b

Reduction factors of the tested solutions

| Beispiel-Nr. | Candida albicans | | | |
|---|---|---|---|---|
| | Belastung | Konz. [%] | 30" | 60" | 120" |
| V6 | clean | 50 | <0.89 | 1.17 | 2.25 |
| E | clean | 50 | | 1.24 | 3 | 6.2 |
| V7 | clean | 50 | | | <0.72 |
| V8 | clean | 50 | <0.89 | 1.33 | 2.34 |
| F | clean | 50 | | 3.05 | 5.72 | >6.37 |
| V9 | dean | 50 | | | <0.63 |

| German | English |
|---|---|
| Beispiel Nr. | Example No. |
| Belastung | Load |
| Konz. | Conc. |

It can be seen, even as regards the fungicidal effectiveness, that the combination of the decontamination agent with an active substance results in a surprisingly strong improvement of the reduction of *Candida albicans*. This improvement is due not only to the active substance, that, as results from examples E in comparison to V6 and V7 and F in comparison to V8 and V9, does not display any sufficient effectiveness by itself.

Even the tables 5b and 6b show that when the agent in accordance with the invention is used as a disinfection- and decontamination agent for surfaces and instruments, a more distinct reduction can be achieved after a short acting time of 5 min than the active substance by itself or as a traditional disinfection agent by itself.

TABLE 5b

Reduction factors of a tested agent in accordance with the invention with QAV

| Beispiel Nr. | pH | Anwendungskonz. [%] | Candida albicans 5 min |
|---|---|---|---|
| V10 (Vergleich) | 3 | 0.5 | 2.49 |
| | | 1 | 2.72 |
| | | 2 | 2.99 |
| | | 4 | 3.65 |
| V11 (Vergleich) | 3 | 0.5 | 0.18 |
| | | 1 | 0.27 |
| | | 2 | 0.32 |
| | | 4 | 0.36 |
| G | 3 | 0.5 | 1.59 |
| | | 1 | 3.26 |
| | | 2 | 4.97 |
| | | 4 | 4.97 |

Key:
| German | English |
|---|---|
| Beispiel Nr. | Example No. |
| Anwendungskonz. | Usage conc. |
| (Vergleich) | (Reference) |

TABLE 5a

Compositions of the solutions with QAVs

| Beispiel Nr. | M-Salz [mM] CuCl2 | Vitamin [mM] D-Ascorbinsäure | Tenside [%] | | | Wirkstoffe | | Komplexbildner | Wasser |
|---|---|---|---|---|---|---|---|---|---|
| | | | SDS | Polysorbat 20 | Fettalkoholalkoxylat | BAC | DDAC | Phosphonsäure | |
| V10 (Vergleich) | | | | | 6.00 | 8.00 | 5.00 | 4.00 | ad 100.0 |
| V11 (Vergleich) | 10 | 100 | 0.50 | 0.30 | 6.00 | | | 4.00 | ad 100.0 |
| G | 10 | 100 | 0.50 | 0.30 | 6.00 | 8.00 | 5.00 | 4.00 | ad 100.0 |

Key:
| German | English |
|---|---|
| Beispiel Nr. | Example No. |
| M-Salz | M-salt |
| Tenside | Surfactants |
| Wirkstoffe | Active substances |
| Komplexbildner | Complexing agent |
| D-Ascorbinsäure | D- ascorbic acid |
| Polysorbat 20 | Polysorbate 20 |
| Fettakoholalkoxylat | Fatty alcohol alkoxylate |
| Phosphonsäure | Phosphonic acid |
| Wasser | Water |
| (Vergleich) | (Reference) |

TABLE 6a

Composition of the solutions

| Beispiel Nr. | M-Salz [mM] FeCl3 | Vitamin [mM] D-Ascorbinsäure | Tenside [%] SDS | Polysorbat 20 | Fettalkoho-lalkoxylat | Wirkstoffe Glutardialdehyd | Wasser |
|---|---|---|---|---|---|---|---|
| V12 (Vergleich) | | | | | 0.20 | 30.00 | ad 100.0 |
| V13 (Vergleich) | 10 | 100 | 0.50 | 0.30 | 0.20 | | ad 100.0 |
| H | 10 | 100 | 0.50 | 0.30 | 0.20 | 30.00 | ad 100.0 |

Key:
| German | English |
|---|---|
| Tensides | Surfactants |
| Wirkstoffe | Active substances |
| Beispiel Nr. | Example No. |
| D-Ascorbinsäure | D- ascorbic acid |
| Polysorbat 20 | Polysorbate 20 |
| Fettakoholalkoxylat | Fatty alcohol alkoxylate |
| Glutardialdehyd | Glutaric dialdehyde |
| Wasser | Water |

TABLE 6b

Reduction factors of a tested disinfection- and decontamination agent in accordance with the invention with aldehydes

| Beispiel Nr. | Anwendungskonz. [%] | Candida albicans 5 min | 15 min |
|---|---|---|---|
| | 0.25 | 0.51 | 0.51 |
| V12 | 0.50 | 0.47 | 0.74 |
| (Vergleich) | 1.00 | 0.67 | 1.18 |
| | 2.00 | 2.72 | 3.80 |
| | 3.00 | >4.71 | >4.75 |
| | 0.25 | 0.75 | 0.72 |
| V13 | 0.50 | 0.58 | 0.46 |
| (Vergleich) | 1.00 | 0.31 | 0.45 |
| | 2.00 | 0.39 | 0.34 |
| | 3.00 | 0.33 | 0.25 |
| | 0.25 | 0.55 | 0.61 |
| H | 0.50 | 0.91 | 1.36 |
| | 1.00 | 2.62 | 4.45 |
| | 2.00 | 4.41 | >4.75 |
| | 3.00 | >4.71 | >4.75 |

Key:
| German | English |
|---|---|
| Beispiel Nr. | Example No. |
| Anwendungskonz. | Usage conc. |
| (Vergleich) | (Reference) |

3. Antibacterial Effectiveness

In other tests the antibacterial effectiveness of the disinfection- and decontamination agent in accordance with the invention was tested. The following tables 7a and 7b show in a comparative manner the effectiveness of a pure disinfection- and decontamination agent as well as of the pure active substance in comparison to the agent of the invention against *Proteus mirabilis*.

TABLE 7a

Compositions of the tested substances

| Beispiel-Nr. | M-Salz [mM] FeCl$_{3x}$ 6H2O | Vitamin [mM] D-Ascorbinsäure | Tenside [%] SDS | Wirkstoffe [%] 1,2-Pentandiol | Milchsäure | Wasser |
|---|---|---|---|---|---|---|
| V14 | 0.3 | 3 | 0.5 | | | ad 100.0 |
| J | 0.3 | 3 | 0.5 | 3.00 | | ad 100.0 |
| V15 | — | — | — | 3.00 | | ad 100.0 |
| K | 0.3 | 3 | 0.5 | | 1.00 | ad 100.0 |
| V16 | — | — | — | | 1.00 | ad 100.0 |

Key:
| German | English |
|---|---|
| Beispiel Nr. | Example No. |
| Tenside | Surfactants |
| Wirkstoffe | Active substances |
| D-Ascorbinsäure | D-Ascorbinsäure |
| 1,2-Pentandiol | 1,2-pentane diol |
| Milchsäure | Lactic acid |
| Wasser | Water |

TABLE 7b

Reduction factors against *Proteus mirabilis*

| Beispiel-Nr. | Belastung | Konz. [%] | Proteus mirabilis 15" | 30" | 60" |
|---|---|---|---|---|---|
| V14 | clean | 50 | <0.74 | 1.15 | 1.83 |
| J | clean | 50 | | >6.39 | |
| V15 | clean | 50 | | >0.95 | |
| K | clean | 50 | 1.24 | 3 | >6.2 |
| V16 | clean | 50 | | <0.72 | |

Key:
| German | English |
|---|---|
| Beispiel Nr. | Example No. |
| Belastung | Load |
| Konz. | Conc. |

It is also surprisingly apparent here that the disinfection- and decontamination agent in accordance with the invention has a distinctly increased effectiveness over a pure decontamination agent and also over the pure active substances.

4. Effectiveness Against Biofilm

In order to determine the effectiveness against biofilm the cleaning of biofilm and therefore the reduction of biofilm was tested. The following table shows the composition of the measured agent. The acting time was 30 min. at 25° C.

TABLE 8a

Compositions of the tested substance

| Beispiel-Nr. | M-Salz [mM] FeCl₃ | "Vitamin" [mM] D-Ascorbinsaure | Tenside [%] SDS | Polysorbat 20 | Wasser |
|---|---|---|---|---|---|
| V17 | 10 | 100 | 0.5 | 0.3 | ad 100.0 |

Key:
| German | English |
|---|---|
| Beispiel Nr. | Example No. |
| M-Salz | M-salt |
| Tenside | Surfactants |
| D-Ascorbinsaure | D-ascorbic acid |
| Polysorbat 20 | Polysorbate 20 |
| Wasser | Water |

Table 8b shows that a distinct reduction of biofilm can be achieved when using the agent in accordance with the invention as a disinfection and decontamination agent for surfaces and instruments after an acting time of 30 min. already.

TABLE 8b

Production of a disinfection and decontamination agent in accordance with the invention for biofilm

| Beispiel Nr. | Anwendungskonz. [%] | Biofilm 30 min |
|---|---|---|
| V17 | 100 | 98.8% |

Key:
| German | English |
|---|---|
| Beispiel Nr. | English No. |
| Anwendungskonz. | Usage conc. |

Thus, the agent in accordance with the invention surprisingly displays a good effectiveness against bacteria, fungi, yeasts and viruses as well as against biofilm. The nucleic acid degradation by the addition of the antimicrobial active substance is unexpectedly improved even more so that the agent in accordance with the invention simultaneously disinfects and decontaminates animated as well as inanimate surfaces.

As can also be gathered from the examples, a special synergism is produced here between the active substance and the base composition of metal salt, vitamin and surfactant that cannot be derived from the behavior of the individual substances. This synergism makes possible an effectiveness at lower concentrations and as a result a better compatibility.

The invention claimed is:

1. A method for the decontamination and disinfection of animate surfaces, comprising applying an effective amount of the composition (i) vitamin C, (ii) between .01-100 mM of a metal ion $FeCl_3$, or $CuCl_2$, (iii) at least one surface-active compound and (iv) at least one antimicrobial active substance, selected from the group consisting of ethanol, 1-propanol, 2-propanol, lactic acid, benzalkonium chloride, didecyldimethyl ammonium chloride, glutaric dialdehyde 1,2-pentane diol, or a mixture thereof.

2. The method according to claim 1, wherein the animated surface is selected from the group consisting of skin, hairs mucous membranes, wounds, or hands.

3. A method for the decontamination and disinfection of inanimate surfaces, comprising applying an effective amount of the composition (i) vitamin C, (ii) between .01-100 mM of a metal ion $FeCl_3$, or $CuCl_2$, (iii) at least one surface-active compound and (iv) at least one antimicrobial active substance, selected from the group consisting of ethanol, 1-propanol, 2-propanol, lactic acid, benzalkonium chloride, didecyldimethyl ammonium chloride, glutaric dialdehyde, 1,2-pentane diol, or a mixture thereof.

4. The method according to claim 3, wherein the inanimate surface is a part of an instrument or surfaces.

5. A method for the production of an agent for the degradation of biofilm an effective amount of the composition comprising (i)vitamin C, (ii) between .01-100 mM of a metal ion $FeCl_3$, or $CuCl_2$, (iii) at least one surface-active compound and (iv) at least one antimicrobial active substance, selected from the group consisting of ethanol, 1-propanol, 2-propanol, lactic acid, benzalkonium chloride, didecyldimethyl ammonium chloride, glutaric dialdehyde, 1,2-pentane diol, or a mixture thereof.

6. The method according to claim 1, wherein the at least one surface-active compound is selected from the group consisting of anionic, non-ionic, amphoteric or cationic surfactants, and a mixture thereof.

7. The method according to claim 3, wherein the at least one surface-active compound is selected from the group consisting of anionic, non-ionic, amphoteric or cationic surfactants, and a mixture thereof.

8. The method according to claim 5, wherein the composition additionally contains an antimicrobial active substance which is an alcoholic active substance selected from the group consisting of methanol, ethanol, 1-propanol, 2-propanol, butanol, chlorobutanol, pentanol or hexanol, propylene glycol, polyethylene glycol, triethylene glycol, hexyldiglycol, butylene glycol, pentanediol, hexanediol, heptanediol, octanediol, decanediol, glycerol, 1,2- or 1,3 diols or hexyldiglycol, 2-bromo-2-nitropropane diol, 5-bromo-5-nitro-1,3 dioxane, benzyl alcohol, chlorobenzyl alcohol, phenylethyl alcohol, phenoxy ethanol, 1,2-phenoxypropanol, 1,3-phenoxypropanol or mixtures thereof.

9. The method according to claim 5, wherein the composition additionally contains an antimicrobial active substance which is a formaldehyde eliminator and/or eliminator of dialdehydes.

10. The method according to claim 5, wherein the at least one surface-active compound is selected from the group consisting of anionic, non-ionic, amphoteric or cationic surfactants, and a mixture thereof.

11. The method according to claim 1, wherein metal ion is present in a concentration of between .01-50 mM.

12. The method according to claim 1, wherein the metal ion is present in a concentration of between .01-10 mM.

13. The method according to claim 3, wherein the metal ion is present in a concentration of between .01-50 mM.

14. The method according to claim 3, wherein the metal ion is present in a concentration of between .01-10 mM.

15. The method according to claim 5, wherein the metal ion is present in a concentration of between .01-50 mM.

16. The method according to claim 5, wherein the metal ion is present in a concentration of between .01-10 mM.

* * * * *

UNITED STATES PATENT AND TRADEMARK OFFICE
CERTIFICATE OF CORRECTION

| | | |
|---|---|---|
| PATENT NO. | : 8,999,399 B2 | Page 1 of 1 |
| APPLICATION NO. | : 13/140436 | |
| DATED | : April 7, 2015 | |
| INVENTOR(S) | : Lisowsky et al. | |

It is certified that error appears in the above-identified patent and that said Letters Patent is hereby corrected as shown below:

On the title page item 73 please change "Bose Chemie GmbH" to -- Bode Chemie GmbH --

Signed and Sealed this
Sixth Day of October, 2015

Michelle K. Lee
*Director of the United States Patent and Trademark Office*